United States Patent [19]

Feiler

[11] Patent Number: 5,115,682
[45] Date of Patent: May 26, 1992

[54] CORONARY ARTERY GRAFT FLOW-METER

[76] Inventor: Ernest M. Feiler, 1514 Coral Cove, Champaign, Ill. 61821

[21] Appl. No.: 526,196

[22] Filed: May 21, 1990

[51] Int. Cl.[5] .............................................. G01F 1/00
[52] U.S. Cl. ....................................... 73/861; 73/269; 128/692
[58] Field of Search .................. 73/223, 262, 269, 861; 128/691, 692

[56] References Cited

U.S. PATENT DOCUMENTS

| | | | |
|---|---|---|---|
| T994,001 | 5/1980 | Buckberg et al. | 128/214 R |
| 2,529,937 | 11/1950 | Hale | 73/269 |
| 3,017,885 | 1/1962 | Robicsek | 128/214 |
| 3,030,808 | 4/1962 | Herman | 73/262 |
| 3,690,318 | 9/1972 | Gorsuch | 128/214 E |
| 3,709,222 | 1/1973 | DeVries | 128/213 |
| 3,718,044 | 2/1973 | Joyce, Jr. et al. | 73/223 |
| 3,875,626 | 4/1975 | Tysk et al. | 73/223 |
| 3,896,733 | 7/1976 | Rosenberg | 128/214 R |
| 4,014,329 | 3/1977 | Welch et al. | 128/214 R |
| 4,474,538 | 10/1984 | Schmid-Schonbein et al. | 417/53 |
| 4,547,186 | 10/1985 | Bartlett | 604/4 |
| 4,613,325 | 9/1986 | Abrams | 604/65 |
| 4,938,072 | 7/1990 | Brown et al. | 73/861 |

Primary Examiner—Herbert Goldstein
Attorney, Agent, or Firm—McDermott, Will & Emery

[57] ABSTRACT

A coronary artery graft flow-meter apparatus for insertion into a delivery line for solution to be perfused through a graft after the graft is anastomosed to a coronary artery is disclosed. The apparatus comprises a flow-meter chamber having an upper end and a lower end, the upper end having an inflow port and the lower end having an outflow port. The chamber includes a plastic bag positioned therein which is adapted to communicate with a volumetric container containing the solution. The solution flows from the volumetric container to the plastic bag thereby providing a measurement of the flow rate of the solution through the graft.

7 Claims, 5 Drawing Sheets

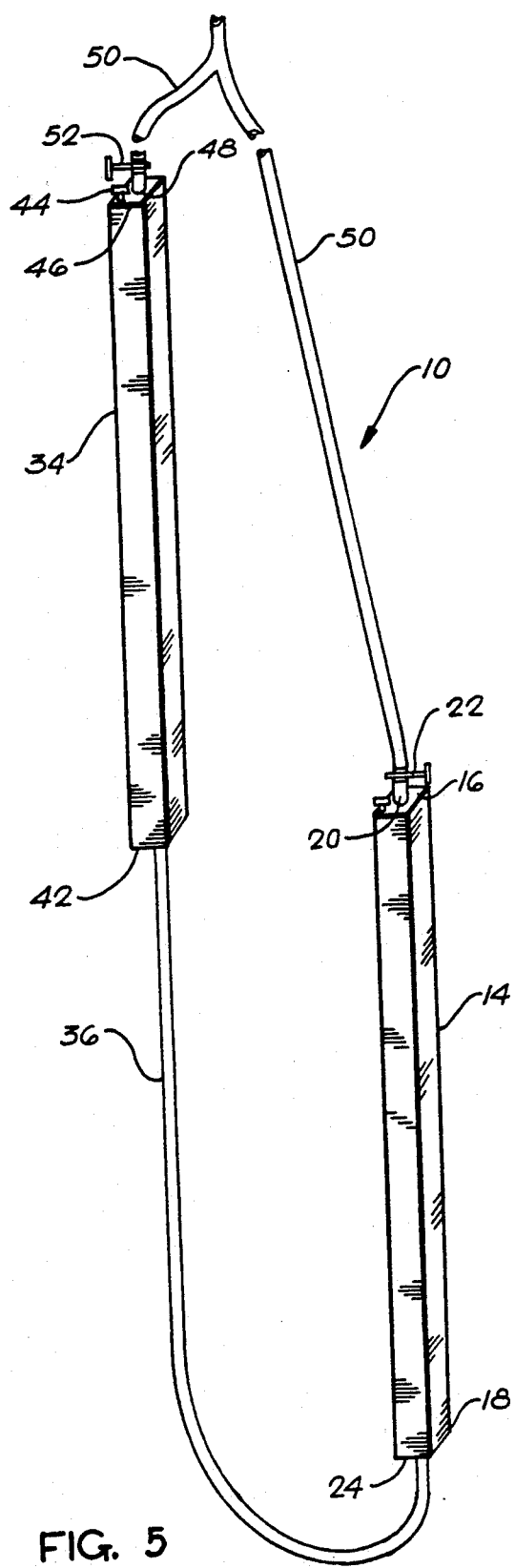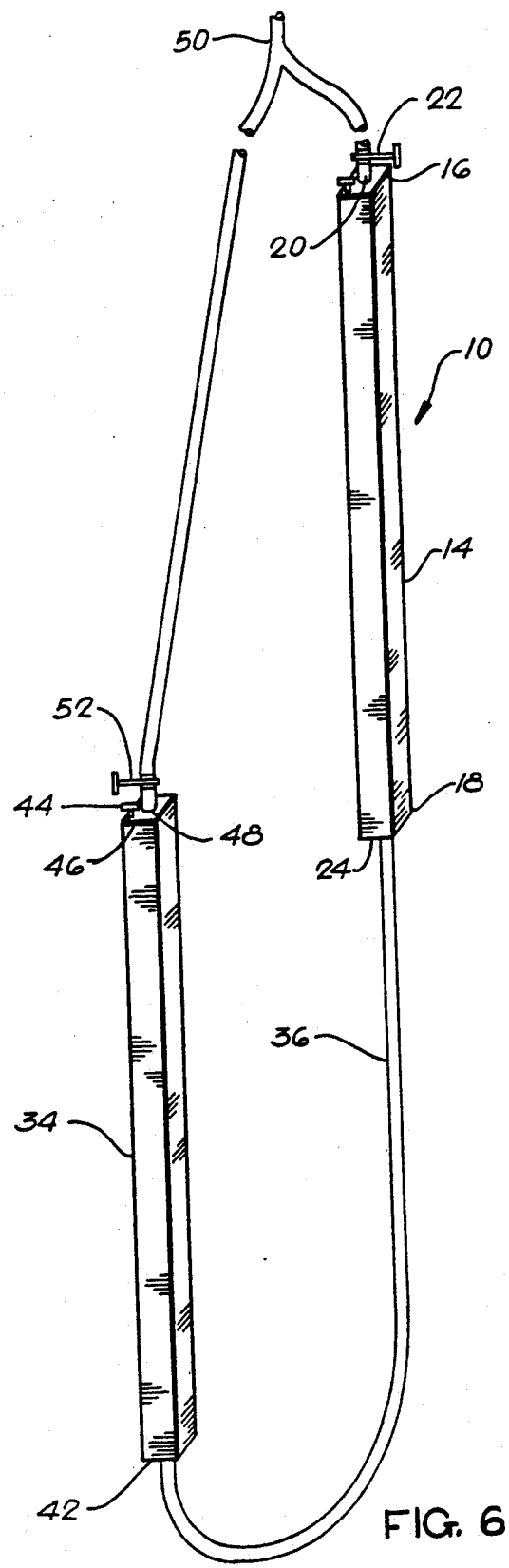
FIG. 5
FIG. 6

CORONARY ARTERY GRAFT FLOW-METER

BACKGROUND OF THE INVENTION

The invention of this application relates to a coronary artery graft flow-meter. More particularly, this invention relates to a coronary artery graft flow-meter apparatus for insertion into a delivery line for solution to be perfused through grafts after the grafts have been anastomosed to coronary arteries.

Indirect flow-meters for coronary artery grafts have been notoriously unreliable and most open-heart surgery centers no longer use them. Direct flow-meters have the disadvantage of possible contamination and/or air embolization. Consequently, there has been a substantial need for a device which is able to overcome both of these possible sources of danger and which would provide a disposable, low-volume closed system that can be inserted into the delivery line for the cardioplegia solution or cold solution which is perfused through grafts after they have been anastomosed to the coronary arteries.

Various flow-rate sensing systems and auto-transfusion systems have been previously suggested. Abrams, U.S. Pat. No. 4,613,325, describes a flow-rate sensing device for use in regulating the rate of flow in a system for parenteral administration of liquids to patients. The liquid emerges from a storage reservoir and is fed into a housing through an upstream flow passage portion and is then made to pass through a narrow flow passage wherein the velocity of the liquid increases while its pressure decreases. The liquid then emerges into a downstream flow-through passage and flows through an outlet from the housing. A pressure transducer, consisting of two chambers separated by a resilient deformable diaphragm, has its upstream chamber in fluid pressure communication with the upstream flow path portion and its downstream chamber in fluid and pressure communication with the flow emerging from the throat passage. Variations of the flow rate through the throat passage effect changes in the pressure differential between the transducer chambers and thus cause variable degrees of displacement of the transducer diaphragm.

Bartlett, U.S. Pat. No. 4,547,186, describes a system for autotransfusion which has an aspirating wand or tube coupled to a vacuum source through a reservoir for receiving aspirated blood. Blood flows from the reservoir to a receiving bag in a relatively low position below the elevation of the patient. When there is sufficient blood supply in the bag, it is elevated from this lower position to a point higher than the patient. Blood then flows from the elevated bag by gravity through a conducting tube and a needle into the patient.

Schmid-Schonbein et al., U.S. Pat. No. 4,474,538, describes a method of circulating organo-biological fluids wherein a fluid contained in a reservoir is released to a pressure level lower than its original fluid pressure level. Thereafter, it is raised periodically to a pressure level above the original level, then transferred from such level to a reservoir position at a predetermined, relatively lower pressure level. It is then drained to an outlet position approximately at the level of the original pressure level.

Welch et al., U.S. Pat. No. 4,014,329, describes a method and device for autotransfusion of blood during surgery. Shed blood is retrieved from a surgical field via a receiving vessel located within a vacuum chamber and under less vacuum than the vacuum applied to the chamber. The vacuum and receiving vessel draw blood from the surgical field into the receiving vessel where it is first collected and then passed to a second vessel. The blood is transferred from the second vessel to the patient during reinfusion.

Rosenberg, U.S. Pat. No. 3,896,733, describes a continuous-flow two reservoir fluid or blood-feed system for administration of fluids to patients. The apparatus is composed of two reservoirs each filled by way of check valves from a common supply and having common connections to a vacuum line. Application of vacuum draws the fluid from the supply line into one of the reservoirs, while fluid is led from the other reservoir to the patient.

DeVries, U.S. Pat. No. 3,709,222, describes a method and apparatus for automatic peritoneal dialysis which includes a series of steps for the exchange of dialysate which proportions the in-flow to the out-flow and provides for the elimination of any distressing in-flow or out-flow pressures on the patient and any abnormal build-up of fluid quantity in the patient. The apparatus includes a portable bed-side unit which carries the necessary pumps and valves for the automatic cycle. It includes a disposable sheet unit supported on the apparatus which is positioned such that pumps and valves in the apparatus can operate on the unit when it is in place.

Gorsuch, U.S. Pat. No. 3,690,318, describes an apparatus which is mounted adjacent to a patient which supports an inspection chamber at a predetermined elevation with respect to the patient. The chamber is connected to the patient through an infusion supply tube. Intravenous infusion fluid is supplied from a container to the inspection chamber at a predetermined pressure and a selected rate. Fluid level sensors give warning if the fluid level in the inspection tube rises or falls a preselected amount.

Robicsek, U.S. Pat. No. 3,017,885, describes means for measuring the flow of blood through an artificial heart-lung pumping system. The means comprise a blood flow meter which is attached directly to a conduit through which blood flows from the heart-lung pump to the patient. It includes means for measuring the drop in fluid pressure as the blood flows through a constriction in the conduit. The pressure drop therein is said to be proportional to the rate of flow of the blood.

Buckberg et al., U.S. Defensive Publication No. T994,001, describes a delivery system for injecting a cardioplegic solution made up mostly of a patient's own blood into his or her heart in order to arrest it. The delivery system is used in combination with a cardiopulmonary by-pass apparatus. The delivery system includes a blood bag for storing a portion of the patient's blood, a Y-shaped tubing having a first end with a single opening and a second end with a pair of openings with the single end mechanically coupled to an oxygenator so that the blood will travel from the oxygenator to the Y-shaped tubing, and a heat exchanger disposed between the blood bag and one of the pairs of openings of the second end of the Y-shaped tubing and connected thereto so that blood may be pumped from the oxygenator through the heat exchanger into the blood bag by a first small roller pump.

Heretofore, none of the flow rate systems for coronary artery grafts provided reliable and safe measurements of the rate of flow through such grafts. The invention disclosed herein comprises a coronary artery graft flow-meter apparatus for insertion into a delivery line for solution to be perfused through a graft after the graft has been anastomosed to a coronary artery or arteries and which provides a measurement of the flow rate of the solution through the graft.

SUMMARY OF THE INVENTION

The present invention contemplates a coronary artery graft flow-meter apparatus for insertion into a delivery line for solution to be perfused through grafts after the grafts have been anastomosed to coronary arteries.

In one aspect of the present invention, the coronary artery graft flow-meter apparatus of the invention comprises a flow-meter chamber having an upper end and a lower end. The upper end has an in-flow port and the lower end has an outflow port therein, which is connected to a pump. The flow-meter chamber includes a plastic bag positioned therein which is adapted to communicate with a volumetric container containing solution, such as cardioplegia solution. The solution flows from the volumetric container to the plastic bag thereby providing measurement of the flow rate of the solution through the graft.

In a further aspect of the present invention, the plastic bag of the coronary artery graft flow-meter apparatus of the invention is collapsible and contains a multifenestrated tube which is capable of filling and emptying the bag.

In another aspect of the present invention, the volumetric container and flow-meter chamber of the graft flow-meter apparatus of the invention are retained on opposite sides of positioning means which are rotatable clockwise and counter-clockwise to raise and lower the volumetric container and flow-meter chamber, respectively.

The present invention provides several benefits and advantages.

One benefit of the present invention is that the graft flow-meter apparatus of the invention can be inserted into the delivery line for the cardioplegia solution which is perfused through grafts after they have been anastomosed to coronary arteries.

Another benefit of the present invention is that the graft flow-meter apparatus of the invention provides a reliable and safe measurement of the flow rate of cardioplegia or cold solution through a coronary artery graft.

One of the advantages of the present invention is that the graft flow-meter of the present invention is a disposable, low-volume closed system.

Another advantage of the present invention is that the graft flow-meter apparatus of the invention is reliable and accurate and minimizes the possibility of contamination or an air embolism occurring.

Other benefits and advantages of the present invention will become readily apparent to those skilled in the art from the following detailed description of the invention, the drawings and the appended claims.

BRIEF DESCRIPTION OF THE DRAWINGS

In drawings forming a portion of the disclosure of this invention:

FIG. 5 is a perspective view of the graft flow-meter apparatus of the present invention illustrating the effect of rotating the positioning means in a clockwise manner;

FIG. 6 is a perspective view of the graft flow-meter apparatus of the present invention illustrating the effect of rotating the positioning means in a counter-clockwise manner.

DETAILED DESCRIPTION OF THE INVENTION

Figure 1:
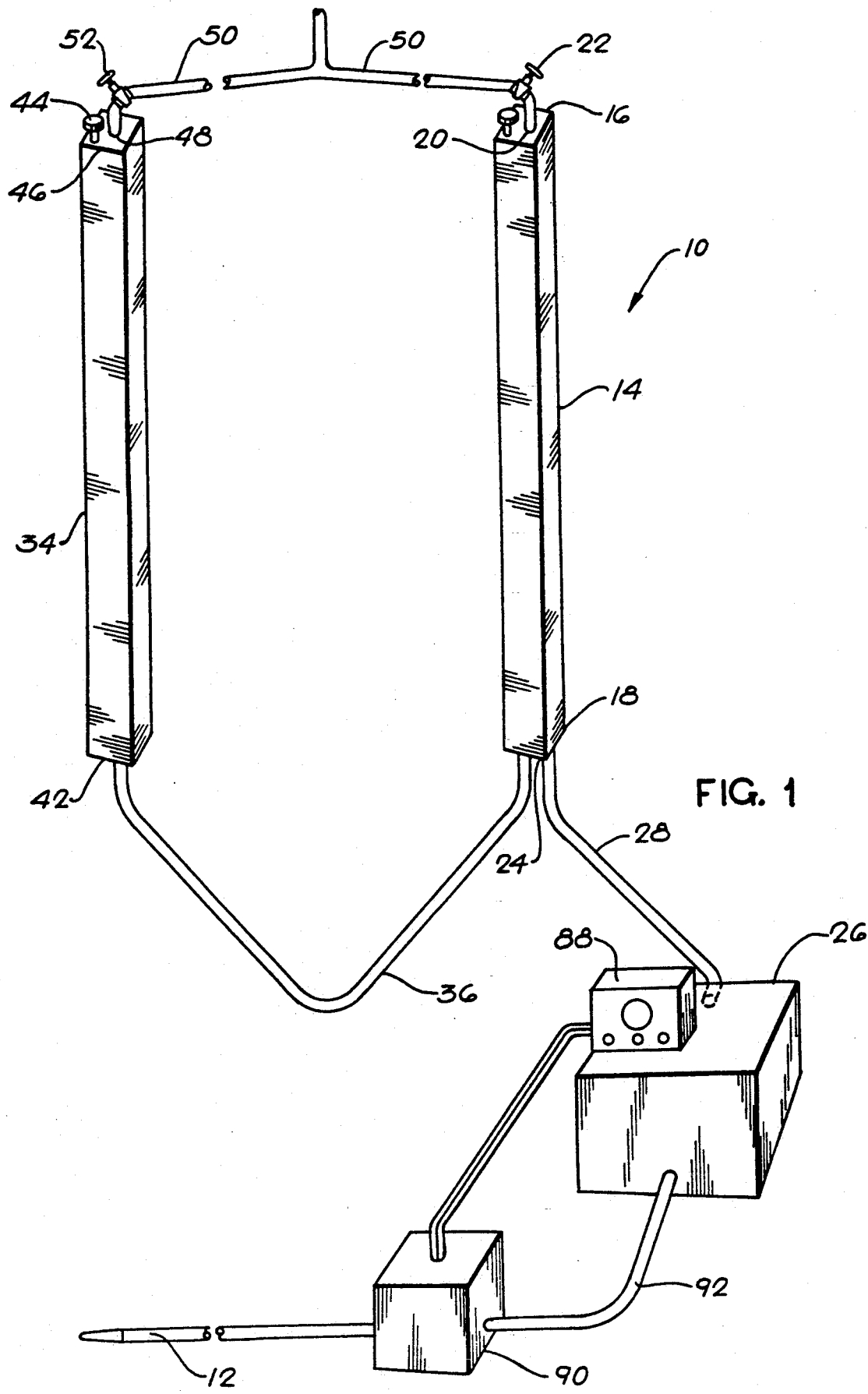
FIG. 1 is a perspective view of the coronary artery graft flow-meter apparatus of the present invention.

The present invention is directed to a coronary artery graft flow-meter apparatus for insertion into a delivery line for solution to be perfused through a graft after the graft has been anastomosed to a coronary artery.

With general reference to FIGS. 1-7, a preferred embodiment of the coronary artery graft flow-meter apparatus of the present invention is shown. The coronary artery graft flow-meter apparatus 10 may be inserted into a delivery line 12 for solution to be perfused through a graft. The flow-meter apparatus 10 comprises a flow-meter chamber 14 having an upper end 16 and a lower end 18. Flow-meter chamber 14 preferably has a volume of 200 cubic centimeters (cc). Upper end 16 has an inflow port 20, secured by a clamp 22 and lower end 18 has an outflow port 24. Outflow port 24 is connected to a pump 26 by means of flow tubing 28.

The flow-meter chamber 14 includes a collapsed plastic bag 30, which preferably has a volume of 160 cc positioned therein. Plastic bag 30 is adapted to communicate via a port 32 with a volumetric container 34. Volumetric container 34 is filled with whatever solution, such as cardioplegia or cold solution, the surgeon desires, as long as the same solution is present in the flow-meter chamber 14. Such solution flows from volumetric container 34 to plastic bag 30 within chamber 14 via flow tubing 36 through port 32. As described in detail hereinafter, this flow mechanism provides a measurement of the flow rate of the solution through the graft.

Figure 2:
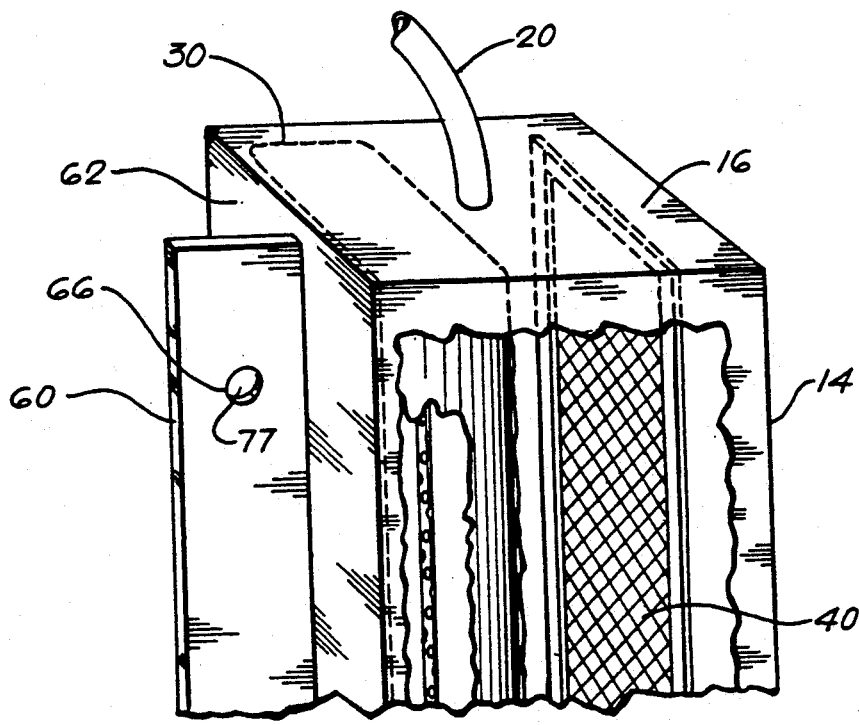
FIG. 2 is a perspective view of the upper end of the flow-meter chamber of the graft flow-meter apparatus of the present invention.
Figure 3:
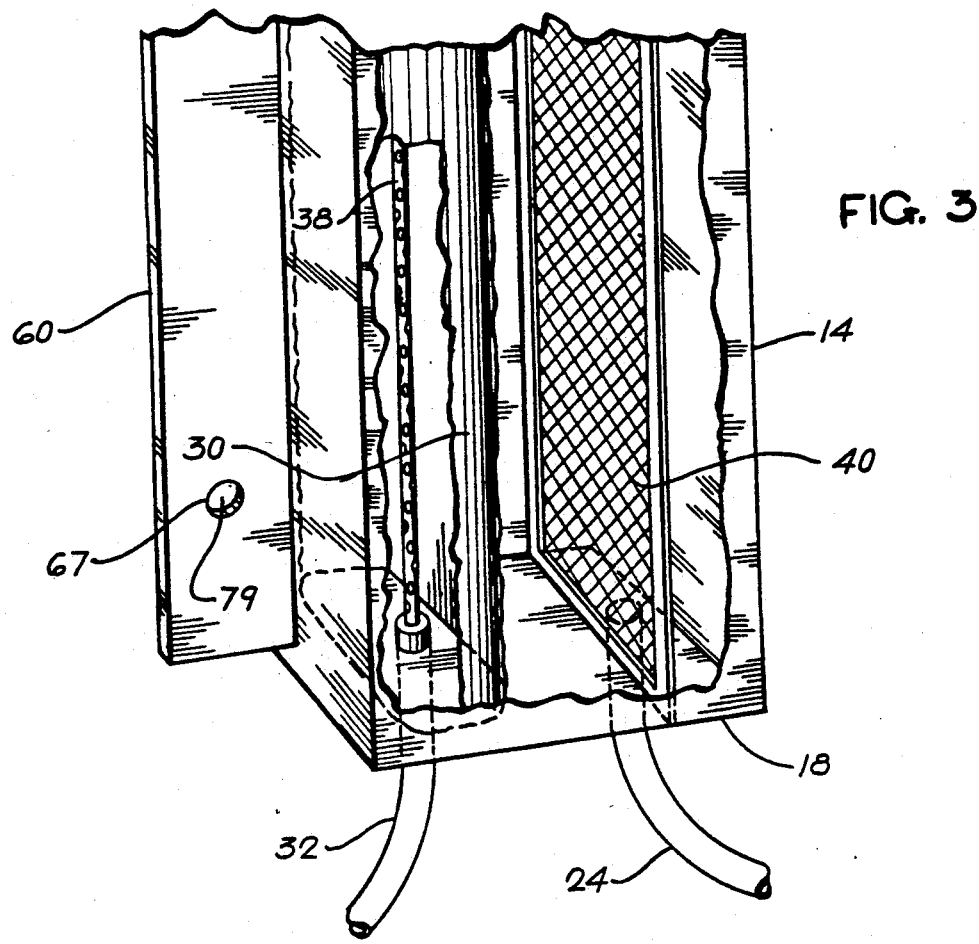
FIG. 3 is a perspective view of the lower end of the flow-meter chamber of the graft flow-meter apparatus of the present invention.

As shown in detail in FIGS. 2 and 3, plastic bag 30 within flow-meter chamber 14 is filled and emptied by a multifenestrated tube 38 within it so that the open end of bag 30 cannot be emptied first and collapse, thereby shutting off the outflow and leaving the closed end of bag 30 without a way to be emptied. Chamber 14 further includes a fence 40 which holds back the plastic bag 30 so that it cannot expand over the outflow port 24 of chamber 14 and shut it off.

Volumetric container 34 preferably has the same dimensions as the flow-meter chamber 14. The preferred dimension is 2×2×50 cm.

As shown in FIG. 1, the flow-meter chamber 14 and the volumetric container 34 communicate via flow tubing 36 at their lower ends 18 and 42, respectively. In the flow-meter chamber 14, the communication goes completely into the multifenestrated tube 38 and the plastic bag 30 around it, while in the volumetric container 34, the communication permits free flow into and out of the container 34. The volumetric container 34 additionally has an air vent 44, at its upper end 46, which is attached to an air filter (not shown).

Once the flow-meter chamber 14 has been filled with fluid and air has been evacuated from the flow-meter chamber 14, the volumetric container 34 can be filled and air vent 44 opened so that the fluid from the volumetric container 34 is free to flow into the multifenestrated tube 38 and the plastic bag 30 within the flow-meter chamber 14, and back again. There is an inflow port 48 at the upper end 46 of the volumetric container 34 through which the container 34 is filled by a Y-tube 50, the other part of which is attached to the inflow port 20 of the flow-meter chamber 14. Just as the flow-meter inflow port 20, the volumetric container inflow port 48 also is secured by a clamp 52.

Figure 4:
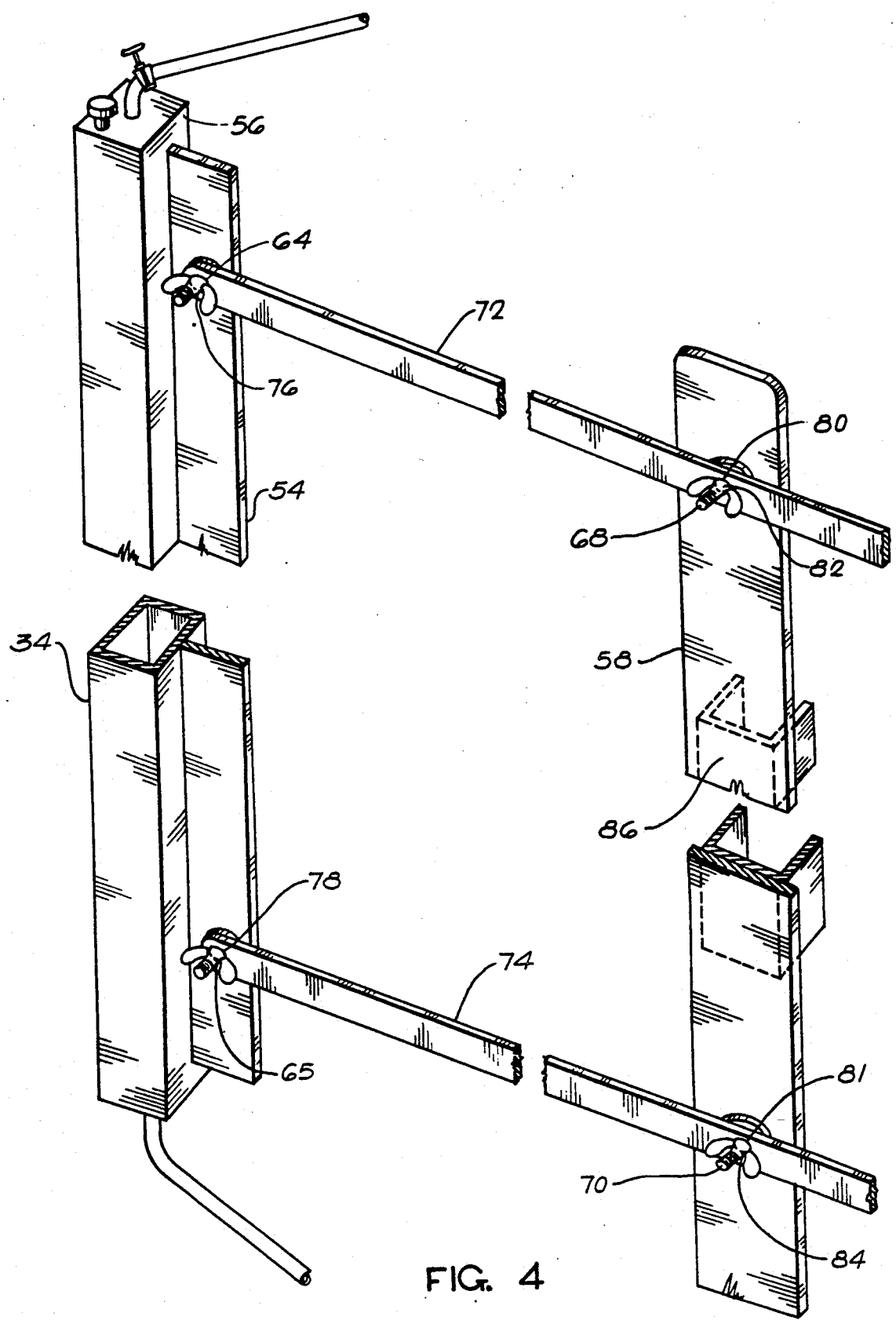
FIG. 4 is a perspective view of the positioning means of the graft flow-meter apparatus of the present invention.

As shown in FIG. 4, the volumetric container 14 is fitted with a bracket 54 on the side 56 facing the flow-meter chamber 14, so that it can be firmly held to a positioning device 58. The flow-meter chamber has a similar bracket 60 on the corresponding side 62.

As shown in FIGS. 5 and 6, the positioning device 58 holds the volumetric container 34 on one side of it and the flow-meter chamber 14 on the other. When the positioning device 58 is rotated clockwise, the volumetric container 34 is raised and the flow-meter chamber 14 lowered so that the apparatus 10 is in the flow-measuring position. When the positioning device 58 is rotated counterclockwise, the volumetric container 34 is lowered and the flow-meter chamber 14 is raised so that the fluid can be emptied more readily from the plastic bag 30 back into the volumetric container 34.

Each bracket 54, 60 is perforated at its upper and lower ends 64, 65, 66 and 67 to fit four pivots, respectively, secured with threaded posts and wing nuts on two strong metal bars 72, 74, with a washer on each side of the bracket. These strong metal bars 72, 74 are attached to a positioning device 58, so that both the volumetric container 34 and the flow-meter chamber 14 can be firmly held on the positioning device 58 with washers and wing nuts.

Figure 7:
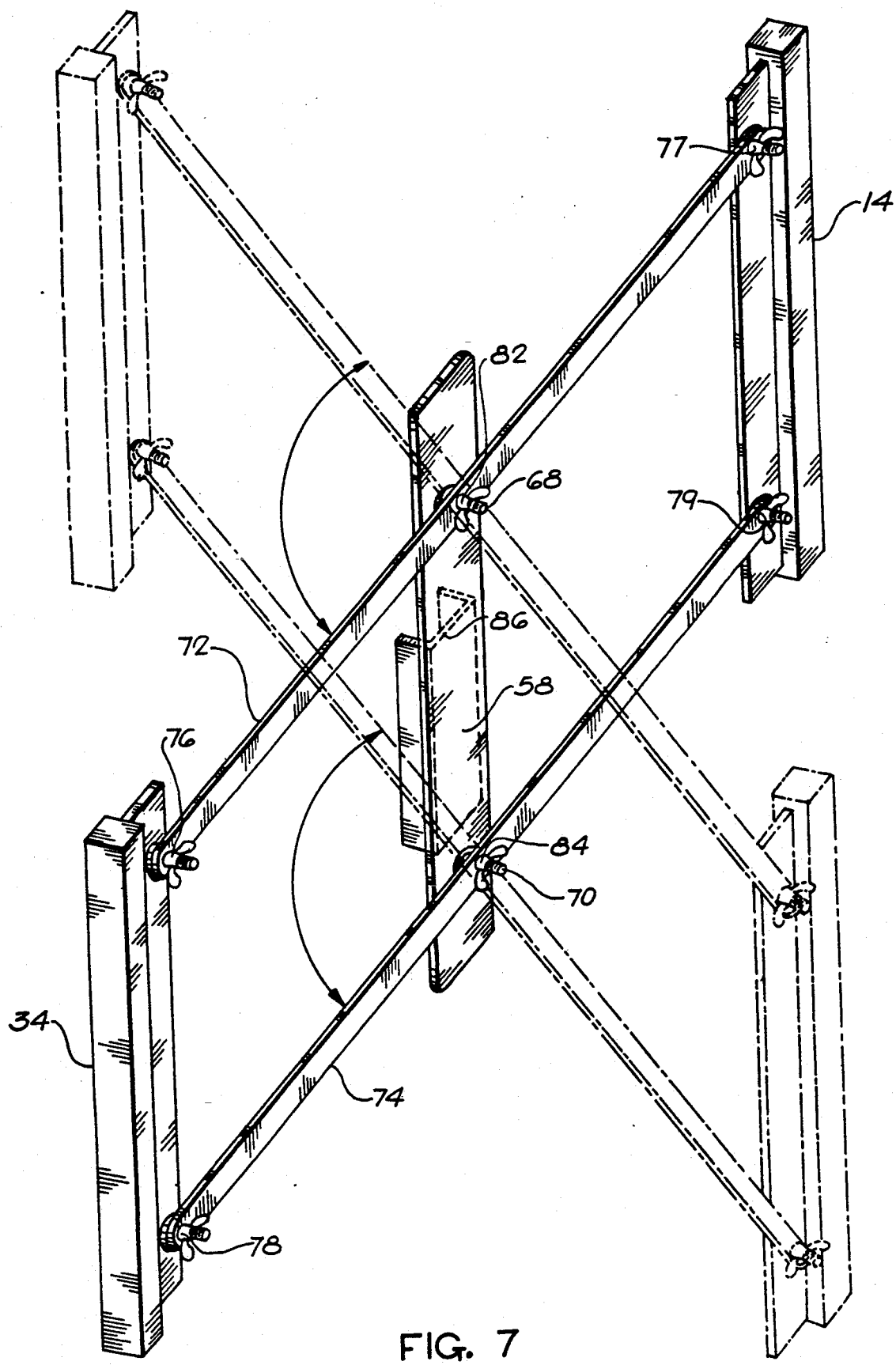
FIG. 7 is a perspective view of the positioning means of the graft flow-meter apparatus of the present invention.

As shown in FIG. 7, attached to each threaded post 68, 70 is a strong metal bar 72, 74, perforated at each end to accommodate a post, with a washer on each side of the metal bar. The upper metal bar 72 that is attached to the upper part 64 of the bracket 54 of the volumetric container 34 is attached at its other end to the upper part 66 of the bracket 60 of the flow-meter chamber 14, and the metal bar 74 attached to the lower part 65 of the bracket 54 of the volumetric container 34 is attached as its other end to the lower part 67 of the bracket 60 of the flow-meter chamber 14.

Halfway between the perforations 76, 77, 78, 79 on each metal bar 72, 74, there are third perforations 80, 81 which permits the metal bars 72, 74 to rotate on pivots 82, 84 respectively. The pivots 82, 84 for the two metal bars 72, 74 are as far apart, one above the other, as the perforations in the brackets, so that the metal bars 72, 74, the brackets 54, 60, and the part 86 of the positioning device 58 between the pivots describe parallelograms with variable angles. In this manner, volumetric container 34 and the flow-meter chamber 14 remain in an upright posture when they are raised or lowered. One metal bar is fitted with a handle (not shown) so that the metal bar can be rotated on the pivot, thereby alternately raising the volumetric container and lowering the flow-meter chamber, and vice versa.

The part 86 of the positioning device between the two pivots 82, 84 is fitted on its back side with a bracket (not shown) to permit it to be tightly fastened to a stand or to a pump-oxygenator so that it will not tip or be knocked over by accident.

In practice, cardioplegia solution, with or without blood, or cold solution, or pump solution, as desired by the surgeon, is used to fill the flow-meter chamber 14, and air is evacuated via an air vent from 16, or by inverting the chamber 14. The tubing 28 from the outflow port 24 runs through the pump 26, and then is connected to the proximal end of the graft in the usual fashion as is well known to those of skill in the art. Cardioplegia or cold solution is then perfused as known in the art, ideally at the patient's pre-surgery mean arterial blood pressure. When a measurement is to be taken, the inflow port 20 of the flow-meter chamber 14 is closed off with the clamp 22. As the cardioplegia or cold solution, etc. is pumped out of the flow-meter chamber 14, the solution from the volumetric container 34 flows into the plastic bag 30 within the flow-meter chamber 14. The rate of flow of this solution precisely corresponds to the flow rate through the graft, and thus provides an accurate measurement thereof.

The rate of flow from the volumetric container 34 can be assessed visually, or with a variety of electronic or colorimetric devices well known in the art. After each measurement, the flow-meter chamber 14 is refilled by opening the inflow port 20 of the flow-meter chamber 14 and raising the chamber 14, by means of positioning device 58, to empty the contents of the plastic bag 30 back into the volumetric container 34. Should simultaneous flow rates through two grafts be required, dual systems can be assembled using a second pump head. Should the plastic bag 30 rupture, the solution from the volumetric container 34, which is the same as is in the flow-meter chamber 14, will mix with the flow-meter chamber solution, thereby avoiding problems as far as graft perfusion is concerned. Should the fluid level in the volumetric container 34 fall too low, a sensor (not shown) attached to the volumetric container 34 will alarm and automatically turn off the pump 26 before air can enter the plastic bag 30 within the chamber 14.

Sterility is assured by discarding the unit after each use. The measuring or sensing device which clips on to the volumetric container 34 as well as the positioning device and the clamps can be removed and reused. The apparatus 10 of the invention can be set up by a pump technician before use and handled in the same way as the pump tubing or coronary perfusion lines to ensure sterility.

The rate of flow through the graft is regulated by a servo mechanism 88 attached to the pump 26, which responds to a pressure sensing device 90 in the line 92 immediately beyond the pump 26 and before the graft.

The coronary artery graft flow-meter apparatus of the present invention, when used properly as described above, provides a disposable, low-volume, closed system which efficiently and safely provides an accurate measurement of the solution flow rate through a coronary artery graft.

The foregoing is intended as illustrative of the present invention but not limiting. Numerous variations and modifications may be effected without departing from the true spirit and scope of the invention.

What is claimed is:

1. A coronary artery graft flow-meter comprising:

a flow-meter chamber having an inflow port for receiving a first liquid and an outflow port for expelling said liquid to said artery graft;

means for controlling the passage of said first liquid into said flow-meter chamber;

an inflatable bag located in said flow-meter chamber, volumetric container means for holding a second liquid;

means for transferring said second liquid from said volumetric container means to said inflatable bag, wherein said inflatable bag receives said second liquid when said control means prevents passage of said first liquid into said flow-meter chamber; and means for measuring flow of said second liquid from said volumetric container means to said inflatable bag.

2. The flow-meter of claim 1 further including a pump connected to said outflow port.

3. The flow-meter of claim 2 wherein said first liquid is cardioplegia solution.

4. The flow-meter of claim 3 wherein said liquid transfer means includes a multi-fenestrated tube located in said bag.

5. The flow-meter of claim 4 further comprising positioning means having a first side and a second side, wherein said volumetric container means is retained on said first side and said flow-meter chamber is retained on said second side.

6. The flow-meter of claim 5 wherein said positioning means is rotatable to a first position, thereby raising said volumetric container means and lowering said flow-meter chamber to facilitate measurement of said flow of said second liquid from said volumetric container means to said bag.

7. A method of measuring liquid flow through a coronary artery graft using a flow-meter chamber containing an inflatable bag, said method comprising the following steps:

first, establishing a first liquid flow path from a first liquid reservoir to said inflatable bag;

second, establishing a second liquid flow path through said flow-meter chamber to said coronary artery graft;

third, stopping flow of said second liquid through said flow-meter chamber to thereby start flow of said first liquid from said reservoir to said inflatable bag; and fourth, measuring said first liquid's rate of flow from said reservoir to said inflatable bag.

* * * * *